United States Patent [19]

Kamentsky et al.

[11] Patent Number: 5,523,207
[45] Date of Patent: Jun. 4, 1996

[54] METHOD FOR ACCURATE COUNTING OF PROBE SPOTS IN CELL NUCLEI

[75] Inventors: Louis A. Kamentsky, Boston; Lee D. Kamentsky, Arlington, both of Mass.

[73] Assignee: Compucyte Corporation, Cambridge, Mass.

[21] Appl. No.: 324,265

[22] Filed: Oct. 17, 1994

[51] Int. Cl.[6] .................. C12Q 1/68; F21K 2/00; C07H 21/04; C12N 15/00
[52] U.S. Cl. .................. 435/6; 435/91.1; 435/91.2; 436/501; 436/63; 436/94; 536/24.3; 536/24.32; 250/462.1; 549/223; 935/76; 935/77; 935/78
[58] Field of Search .................. 435/6, 91.1, 91.2; 536/24.3–24.32; 935/76–78; 436/501, 63, 94; 250/462.1; 549/223

[56] References Cited

U.S. PATENT DOCUMENTS 5,072,382  12/1991  Kamentsky .................. 364/413.08

FOREIGN PATENT DOCUMENTS 9306245  1/1993  WIPO .

OTHER PUBLICATIONS

Martin–Reay et al., *American Journal of Clinical Pathology*, vol. 102, No. 4, Oct. 1991, pp. 432–438.
Lichter et al., GATA 8(1):24–35, 1991.

*Primary Examiner*—W. Gary Jones
*Assistant Examiner*—Bradley L. Sisson
*Attorney, Agent, or Firm*—Graham & James

[57] ABSTRACT

A method for the accurate counting of DNA probe spots in cell nuclei wherein anomalies caused by a two dimensional measurement of a three dimensional cell sample are eliminated from evaluation. DNA probe spots in cell nuclei which are counted by means of Fluorescent In Situ Hybridization (FISH) include cells wherein probe spots of different contoured cells are overlaid or are detected as being adjacent one another with resultant erroneous diagnostic results such as with cancer detection or prognosis. A gating fluorescent value is determined by clusters of fluorescence in regions of non-anomalous values of fluorescence determined by plotting peak fluorescent value against area. The loci of the non-anomalous peak values cluster in specifically definable regions whereby fluorescent values for cells which deviate from the gating fluorescent value, are discounted in the preparation of histograms or other diagnostic measurements.

4 Claims, 5 Drawing Sheets

METHOD FOR ACCURATE COUNTING OF PROBE SPOTS IN CELL NUCLEI

FIELD OF THE INVENTION

This invention relates to methods and devices utilized in determining DNA content in cells for diagnostic purposes and specifically relating to methods and devices utilized for counting fluorescent probe spots of DNA sequences in cells.

BACKGROUND OF THE INVENTION

Cytometers, such as described in U.S. Pat. No. 5,072,382, issued to applicant herein, have become a common tool for the examination of biological cell samples for various properties and/or defects indicative of abnormalities and diseases. The cytometers utilize a dye absorption property of DNA and of specific DNA sequences (contained in the cells of the samples), with developed procedures, in order to provide a variety of information relating to the DNA content of the cells. These include degree of anomaly, such as variations in DNA content and its character. The information, so obtained, is important in various diagnoses and treatment such as in cancer detection and treatment and in the prior determination of birth defects such as Down's syndrome and the like.

In one developed procedure (using a cytometer), called fluorescent in situ hybridization (FISH), fluorescent dyes (such as fluorescein isothiocyanate (FITC) which fluoresces green when excited by an Argon ion laser) are used to tag a sequence of DNA which is complementary to a defined nucleotide sequence of DNA in the cell, with the sequences being joined, such that cells with specific DNA sequences can be detected microscopically. Each chromosome containing the target DNA sequence will produce a fluorescent spot in every cell, with scanning of the cells with a laser exciting the dye to fluoresce. Thus, for example, specimens hybridized with a DNA sequence known to be contained on chromosome number 21 will produce two fluorescent spots in cells from normal patients and three spots from Down's Syndrome patients because they have an extra chromosome number 21. A microscope based, stationary sample cytometer, used in this procedure, is disclosed in said US Patent issued to applicant, the disclosure of which is incorporated herein by reference thereto.

Typically, thousands of cells are scanned in a cytometric sample and the specific DNA sequence contents are determined in the form of fluorescent spots, which are counted relative to the number of cells. Deviation of the number of spots in a cell from a norm (e.g., such as probing for X chromosomes on human lymphocytes, based on gender—males having one X chromosome and thus normally one fluorescent spot per cell and females having two X chromosomes and thus normally two fluorescent spots per cell) is indicative of a disease, cancer or other abnormality. The relative number of abnormal cells to the total cell sample population is also indicative of the extent of the condition or abnormality.

An initial technique, described in applicants' co-pending application no. 07/987,679, filed Dec. 2, 1992 (the disclosure of which is incorporated herein by reference thereto) for such probe spot counting determination was the differentiation of fluorescing spots within a single cell as opposed to fluorescing spots of adjacent cells. This technique uses measurement of interspot distances, as an accurate means for discrimination, whereby spots within a single cell are always closer than those of even adjacent cells. Thus, the distance between a probe spot and its Nth nearest neighboring spot are measured. If the spots are close, they are on the same cell. If the distance to the Nth nearest neighboring spot is large, they are on different cells. Large populations of cells can be measured thereby and the numbers of cells for each Nth nearest distance value can be plotted. These distributions can thus be used to characterize the number of spots per cell without actually counting spots within the cell boundary.

In a more recently developed method, a second dye, e.g., propidium iodide (PI) has been utilized to contour the nucleus based on PI fluorescence (which fluoresces red when excited by the Argon ion laser) to define the cell boundary, thereby independently contouring the probe spots and counting probe spots within the PI contour as spots defined within the cell.

However, a problem remains, with both methods, as an artifact of the cytometric analysis equipment being utilized. Cytometers, being depth independent, essentially monitor cell samples in a two dimensional plane whereas cells in a sample are in a three dimensional dispersion. As a result, the three dimensional cell is projected on to a two dimensional area. Cells and probe spots therefore often overlay and can not be separated from each other. It is however, important to be able to eliminate the effect of such overlay since in clinical applications, such as with respect to cancer, a deleted gene is diagnostically important. Two factors are present in the overlay problem which must be accounted for. A first factor is the overlay of the cells and the second being an overly of probe spots within a single cell.

It is accordingly an object of the present invention to provide a method for accurately determining the fluorescing spot count of individual cells in a three dimensional sample matrix utilizing a two dimensional monitoring cytometer.

It is a further object of the present invention to be able to separate overlying probe spots for improved diagnostic determinations.

These and other objects, features and advantages of the present invention will become more evident from the following discussion and drawings in which:

SHORT DESCRIPTION OF THE DRAWINGS

Figure 7A:
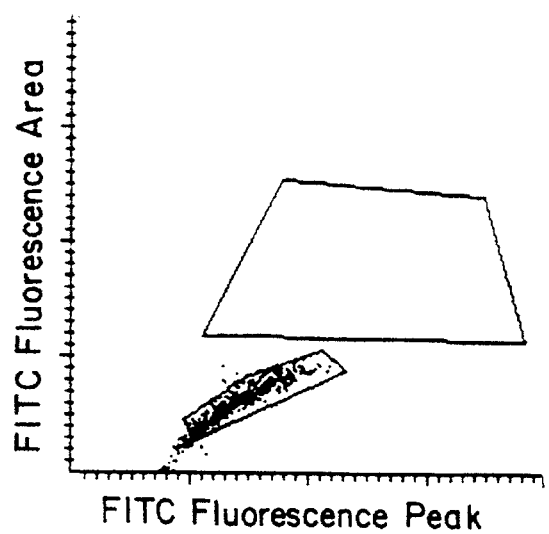
Figure 7B:
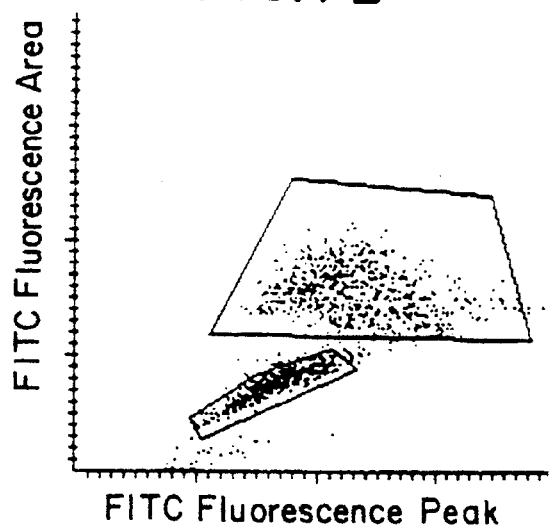

FIGS. 7a and 7b are scattergrams of FITC-probe area plotted versus FITC-probe peak fluorescence with that probe area for the lower male gating region (FIG. 7a) and for the upper female gating region (FIG. 7b), respectively; and FIGS. 8a, 8b, 8c and 8d are graphs showing the distribution of number of cells as a function of the two properties, FITC fluorescence per cell and spot count per cell, for the male lower region (8a), female lower region (8b), female upper region (8c) and all cells (male and female) lower region (8d), respectively.

SUMMARY OF THE INVENTION

Generally the present invention comprises a method for the accurate counting of tagged DNA sequence probe spots in cell nuclei and for the accurate measuring of DNA of fluorescing cell nuclei wherein anomalies caused by a two dimensional measurement of a three dimensional cell sample are eliminated from evaluation. Probe spots in cell nuclei which are counted by means of Fluorescent In Situ Hybridization (FISH) include cells wherein probe spots of the same or different contoured cells are overlaid or are detected as being adjacent one another with resultant erroneous diagnostic results such as with cancer detection or prognosis.

In accordance with the present invention, probe spots are separated, in the three dimensional matrix, in a method for the accurate counting of tagged DNA sequence fluorescing contoured probe spots in fluorescing cell nuclei of a microscope slide sample, wherein anomalies are caused by a two dimensional measurement of the three dimensional cell sample comprising the steps of:

a. plotting peak fluorescent value of each fluorescing probe spot against the area within the contoured probe spot;
  b. determining a gating cluster region of probe spot peak value versus probe spot area within the probe spot contours; and
  c. eliminating from evaluation and counting, cells having probe spots which do not fall within said cluster region.

Similarly, overlapping cell nuclei can be separated and nonisolated cells eliminated from further evaluation and counting by the above steps as applied to the cell nuclear contour and contour area and peak fluorescence of the cell nuclei, which provides cluster regions of isolated cell nuclei.

It has been discovered that the loci of the non-anomalous peak values cluster in specifically definable regions whereby the above steps are effective in eliminating spurious measurement, by the effective separation of overlying probe spots.

It has been discovered that single isolated cells tend to similarly cluster. Accordingly, in the initial steps it is preferred that only the single isolated cells in a cluster, in a determination of PI fluorescence value versus PI fluorescence peak, be further evaluated with probe spot separation as described above.

DETAILED DESCRIPTION OF THE INVENTION THE DRAWINGS AND THE PREFERRED EMBODIMENT

The cytometer described in the aforementioned patent provides results in various formats including scattergrams in which dots are shown on a screen. The dots each represent one cell or a probe spot with coordinates of two measurement properties such as integrated fluorescence, area within a contour (determined by counting pixel points therein), peak fluorescence within the contour, X or Y position, time of measurement, distance to the nearest contour peak or count of contours from one fluorescence color within the contour derived from another fluorescence or scatter measurement. These properties are derived by computer processing of the pixel data points within the appropriate contour.

EXAMPLE

In order to illustrate the operation of the present invention and because of the natural difference of probe spots per cell, the method of the present invention is applied to a known X chromosome probe in a sample of cells comprised of a mixture of cells from a female subject and from a male subject. The cells from the female subject each contain two X chromosomes per cell and each cell should produce two fluorescent spots. The cells from the male subject each contain only one X chromosome and only one fluorescent spot should be produced from each cell thereof.

A sample of the cells, prepared according the FISH procedure, is placed on a microscope slide. The slide sample is then stained with the dye, PI, at a concentration of 0.5 μg/ml which causes the nucleus of a cell to fluoresce red when excited by an Argon ion laser beam. The dye, FITC, used in the FISH technique fluoresces green when excited by the Argon ion laser.

A cytometer is used to scan the slide by imaging an Argon ion laser into a 2 micron diameter spot on the sample. The scan beam is moved 150 microns up and down at a rate of about 100 times per second as the slide is moved perpendicular to the scan, thereby creating a raster strip scan pattern. Microscope stage motion is such that successive scans are spaced 0.5 microns apart. The stage is then moved in the scan direction a distance of 150 microns to scan an additional strip and the process is repeated until a fixed area of the slide is scanned.

During the process, each cell when under the laser beam emits red fluorescent light over its nuclear area projection and green fluorescence light as each FISH treated gene is encountered by the laser beam. The dual fluorescence is collected and detected and digitized. The digitized values of each scan pixel are displayed as a scan data display image in which the brightness of each point in the image is proportional to the value of the pixel. With appropriate software, a closed contour is constructed to surround each cell's pixel set based on the level of PI fluorescence detected, and around each probe based on the level of FITC fluorescence detected. The contours are also displayed on the scan data display.

Figure 1:
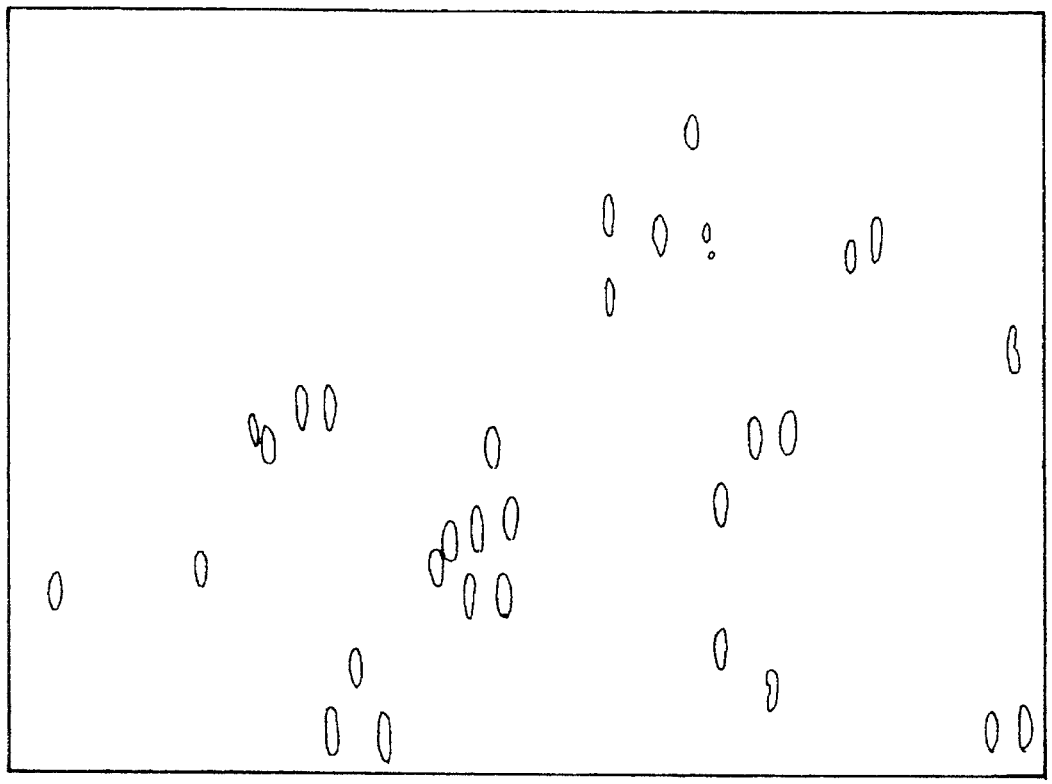
FIG. 1 is a scan display of a red fluorescence PI stain of cell nuclei of mixed male and female cells.
Figure 2:
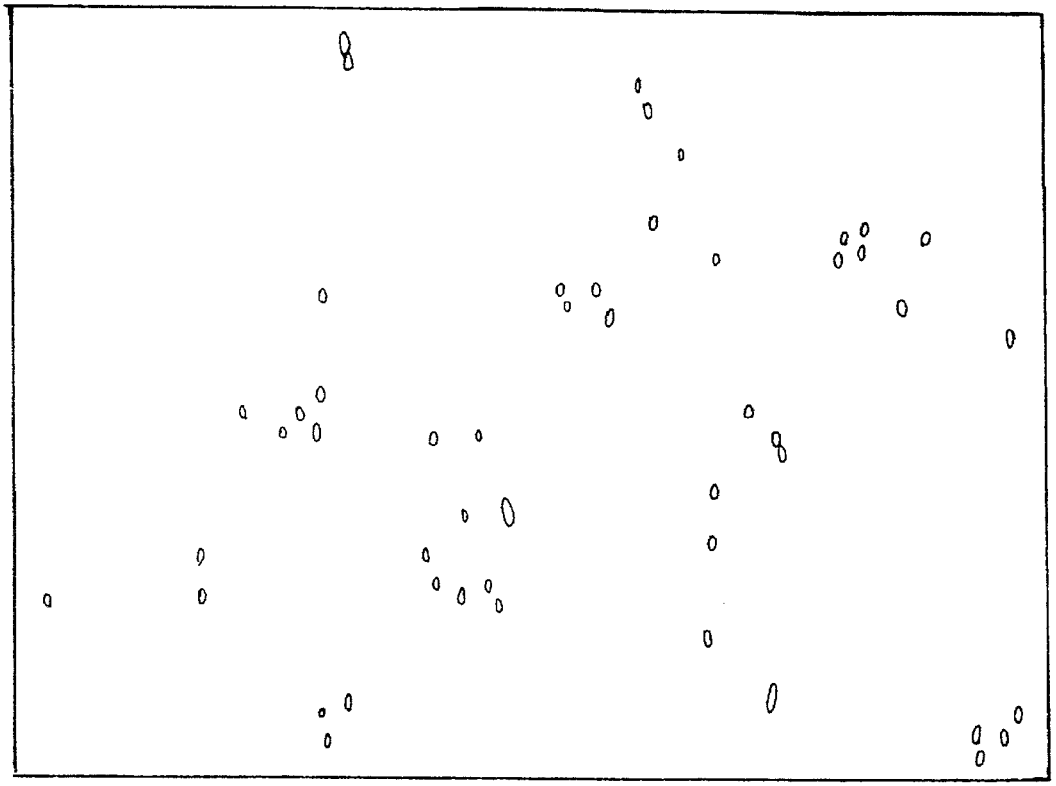
FIG. 2 is a scan display of the same field of FIG. 1 with a green FITC scan display.
Figure 3:
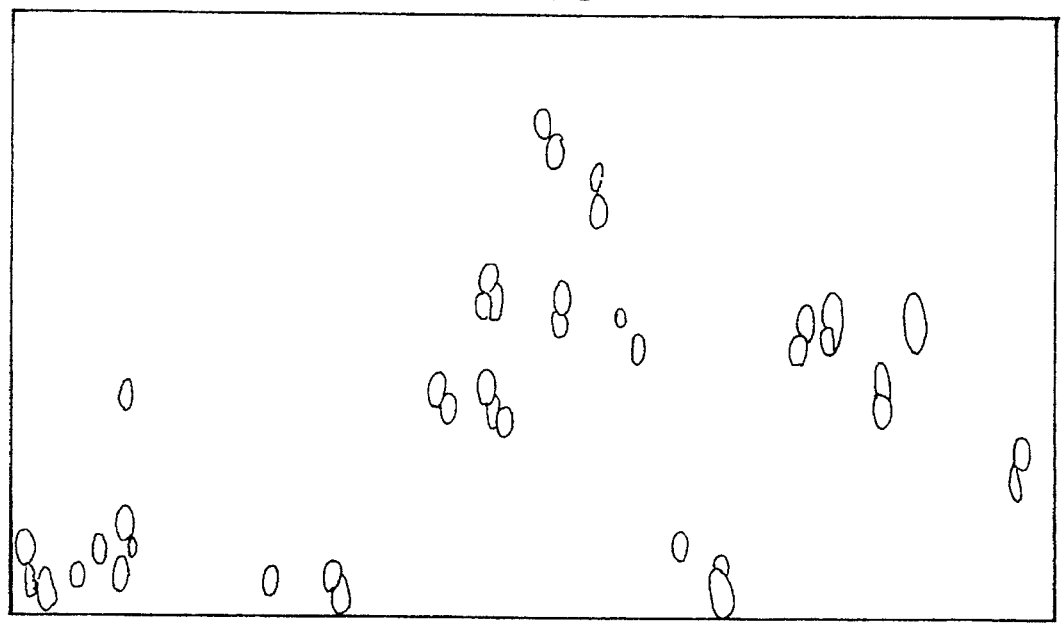
FIGS. 3 and 4 are red fluorescence and green fluorescence scan displays respectively of part of the same field with dual PI/FITC contouring.
Figure 4:
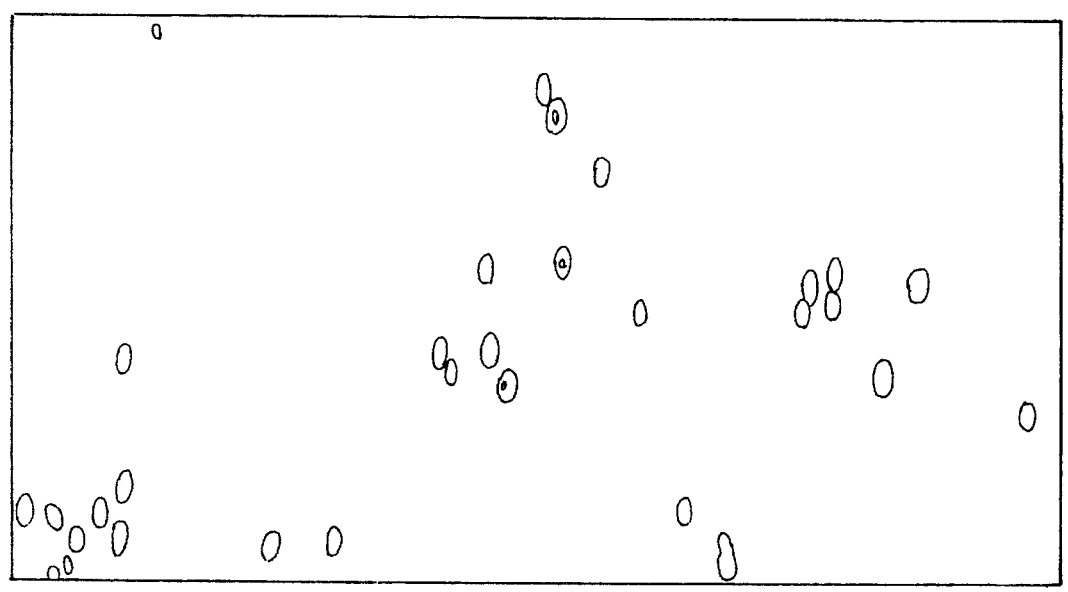

FIGS. 1 and 2 are scan displays of the red fluorescence PI stain of the cell nuclei and green fluorescence FITC respectively. FIGS. 3 and 4 depict the scan displays of FIGS. 1 and 2 with dual PI/FITC contouring. It may be noted that some cells (male) have one probe spot, some cells (female) have two clearly isolated probe spots, and that some cells (female) have two probe spots that overlap and cannot be isolated. The overlapped probe spots, as described above, result from the fact that the cytometer data is a projection of the three dimensional nucleus into a two dimension area.

With a random distribution of the probes in the nuclear volume, projections are very likely to overlap. Thus, with a cell in an unknown specimen (i.e. the number of probe spots not being known) there is a resultant inability to correctly determine the number of spots therein. Thus, it is difficult if not impossible to be certain if a chromosome, or a gene sequence on a chromosome is deleted or mutated since an overlap of probe spots provides the same result as a deletion of a gene.

Figure 6:
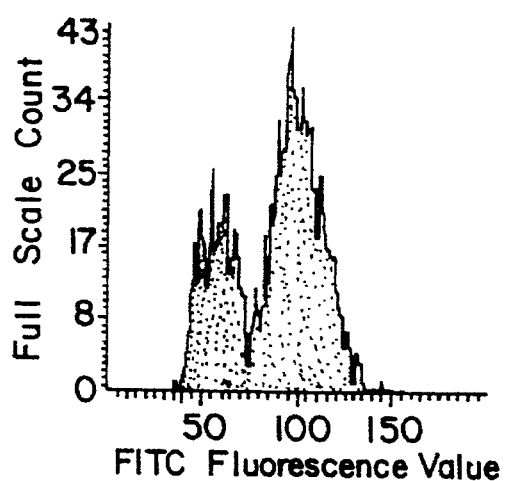
FIG. 6 is a plot of the distribution of the number of cells for each value of green FITC fluorescence.
Figure 5A:
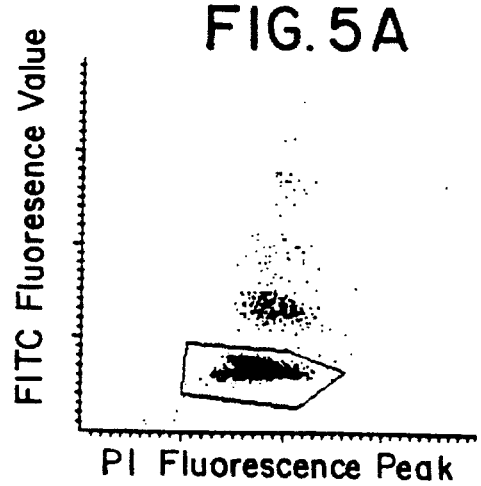
FIGS. 5a and 5b are scattergrams of PI Fluorescence Area versus Peak and FITC value versus PI Fluorescence Value respectively.
Figure 5B:
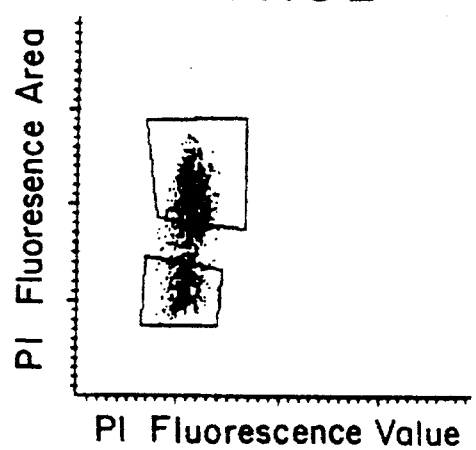

In accordance with the present invention, as described, gating regions are utilized to eliminate cells which have no clear probe spot separation and to eliminate overlapped cells from the evaluation. To this effect, scattergrams shown in FIGS. 5a and 5b are derived from the above illustrative example, using only the PI contour (measurements derived from the total nuclei of each cell). The term "Value" is defined as the sum of all fluorescence in the contour (i.e. PI fluorescence) is proportional to total DNA per cell, "area" is the count of pixels within the contour, and "peak" is the value of the pixel having the largest fluorescence. The boxed areas in each of the scattergrams, referred to herein as "regions" are used to gate events so that a successive scattergram will get data points only from cells in a region of another scattergram, e.g., the scattergram of FIG. 5b shows data points from the "region" of the scattergram in FIG. 5a. Single isolated cells fall within this region. FIG. 6 is a plot of the number of cells for each value of green FITC fluorescence. In the illustrative example, since male cells have one probe spot per cell and female cells have two probe spots per cell, the total FITC fluorescence, per cell, clusters about two values, with one being twice that of the other, as shown in FIG. 6.

FIGS. 7a and 7b are two scattergrams of FITC-probe area plotted against FITC-probe peak fluorescence within that probe area, with the first (FIG. 7a) being derived from the lower (male) gating region and the second (FIG. 7b) being derived from the upper (female) gating region of the FITC versus PI scattergram using the PI contour (FIG. 5b).

In FIG. 7a, of probe spot area-peak measurements, from male cells, there is a single spot cluster and in FIG. 7b, from female cells there are two clusters, a first in a position similar to that of male cells (single spot cluster) and a second more diffuse cluster, which in the case of female cells is due to overlapping probe contours. This results in a large probe contour area or a high peak fluorescence if parts of the probe overlay to a greater extent.

The software excludes from further processing all cells not within the gate region of FIG. 5a. The software further excludes processing of cells having any probe spot area peak values outside the gating region in use in FIG. 7a or 7b.

Figure 8B:
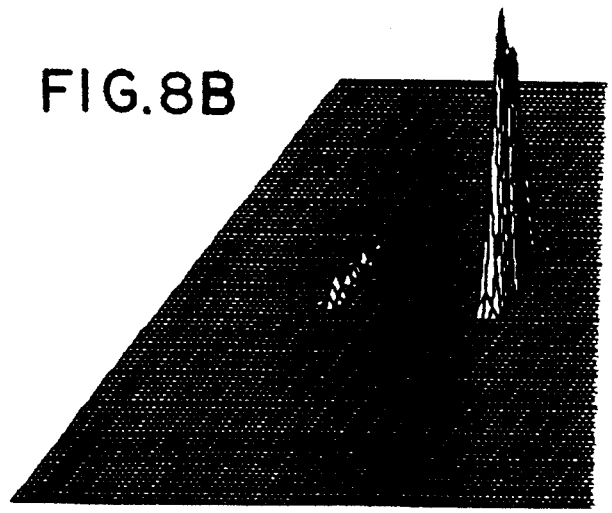
Figure 8A:
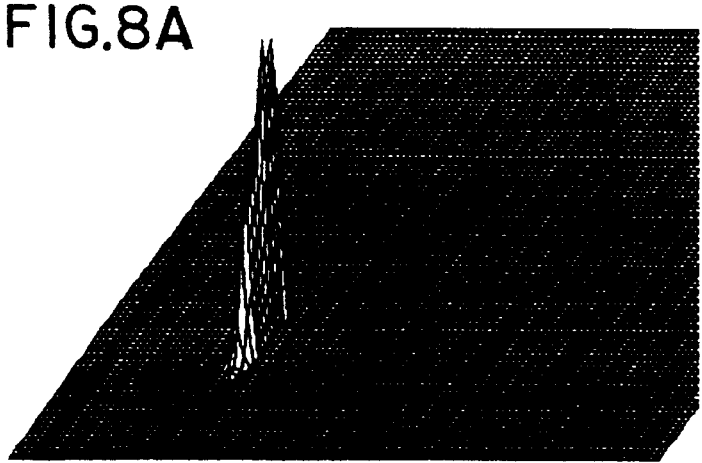
Figure 8C:
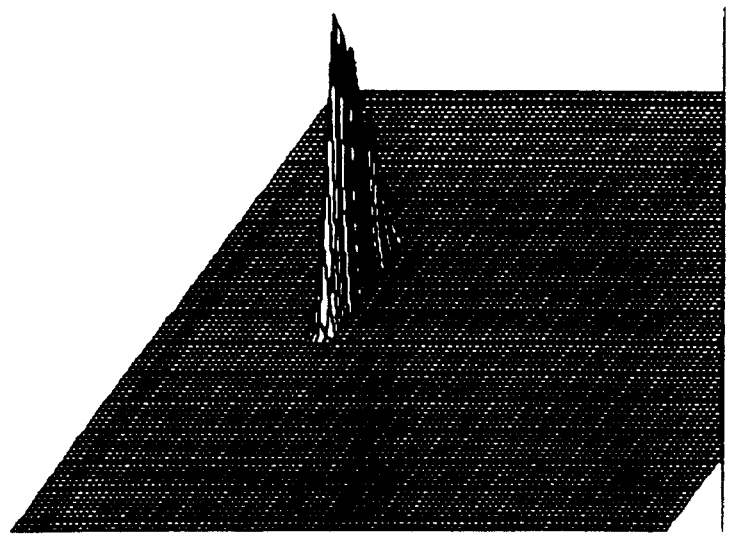
Figure 8D:
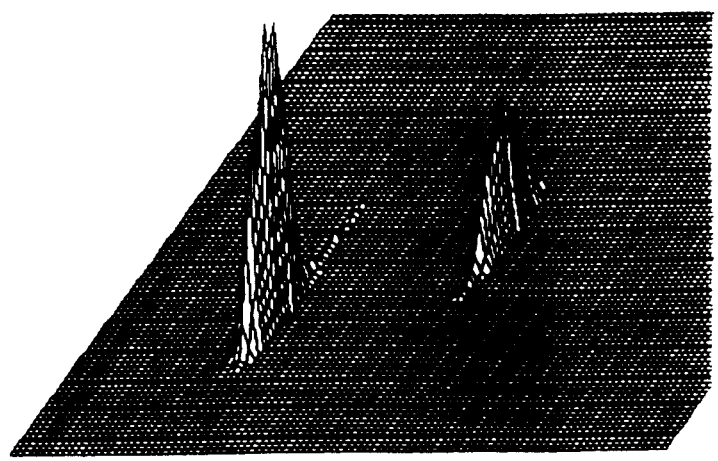

Appropriate software is used to count FITC-probe spots within the PI contour on the two gating regions and FIGS. 8a-d are graphs showing the distribution of the number of cells as a function of the two properties, FITC fluorescence per cell and spot count per cell. FIG. 8a shows the male lower region of FIG. 7a and FIG. 8b shows the female lower region of FIG. 7b. FIG. 8c depicts the Female upper region and FIG. 8d is a composite of all cells (male and female) in the lower region.

The spot count per cell of the upper diffuse region is one, despite the fact that the cells are predominately female and should have contained two spots. These cells accordingly contain improperly segmented FITC contours. However, the three graphs of FIGS. 8a, 8b, and 8d showing the lower region show proper results in that the predominately male cells have a count of one and the predominately female cells have a count for almost all cells of two. The mixed population graph of FIG. 8d shows the cells with the one count cluster at a lower FITC value than the cells with a two count cluster. The cells of FIG. 8c are therefore discounted in further evaluations of the cell sample.

The determination of the gating region can be made by examining a large number of cells. Isolated single cells generally form a condensed cluster of points when peak fluorescence within the nuclear boundary contour is plotted versus area of the nuclear contour. Isolated single probe spots generally form a condensed cluster of points when peak fluorescence within the probe spot boundary contour is plotted versus area of the probe spot contour. In each case, with appropirate sopftware, a gating region containing the condensed cluster can be drawn on the computer screen scattergram of nuclear peak value versus nuclear area and can be drawn on the scattergram of probe spot peak value versus probe spot area, using a "mouse", so that only single isolated cells will be further processed, and probe spots will be counted only for cells in which all of the probe spot peak versus area values are within the probe scattergram gating region.

In view of the above illustrative Example, it is evident that the clustering effect of probe spots within a specific region, as well as single isolated cells falling within a similar type of clustering region, serves to provide a basis for accurate counting of isolated probe spots (and the specifically tagged nucleitide sequence) as well as for separation of isolated cells. From the above Example, FIG. 8d provides the basis for the appropriately counted cell spots It is understood that the above description and exemplification of the present invention is only exemplary thereof and that details contained therein are not to be construed as limitations on the present invention. Changes in means for tagging DNA sequences as well as detection, and the like, may be changed or modified without departing from the scope of the present invention as defined in the following claims.

What is claimed is:

1. A method for accurate counting of tagged DNA sequence fluorescing probes within fluorescing cells or cell nuclei of a microscope slide specimen, wherein anomalies in said counting are caused between a cell specimen having three dimensions, in which said cells or cell nucleii are positioned, and a counting measurement effected in only two of the three dimensions, the method comprising the steps of:

a) illuminating the specimen with light so as to cause fluorescence emission from the cells;

b) detecting and representing the positional values of intrinsic or dye bound fluorescent emission of the cells or their nucleus as an array of digital values, c) detecting at least one fluorescent emission resulting from a dye tagging a probe bound to a nucleic acid sequence in the cells and representing the positional values of fluorescent emission of the probes as an array of digital values;

d) defining a digital contour surrounding each cell or cell nucleus based on the digital values resulting from the cells or their nuclei;

e) within each cell or nuclear contour, defining a second set of digital contours surrounding each probe based on the digital values resulting from the probe fluorescence;

g) computing the area of each probe spot by counting numbers of pixels within its contour;

h) finding the maximum fluorescent value within each probe contour; and i) defining a subset of values of probe area versus probe maximum fluorescence within the total range of area and maximum values; and j) eliminating from evaluation and counting cells if any of their set of probe area and maximum values which do not correspond to any of the subset of values.

2. The method of claim 1, wherein the probe spots result from cells treated by means of fluorescent in situ hybridization (FISH).

3. The method of claim 3, wherein a predetermined DNA sequence in said sample is dyed with fluorescein isothiocyanate.

4. The method of claim 3, wherein the slide sample is stained with propidium iodide.

* * * * *